(12) United States Patent
Halbert et al.

(10) Patent No.: US 9,586,001 B2
(45) Date of Patent: Mar. 7, 2017

(54) ADAPTIVE VOLUME PER MOTOR REVOLUTION SYSTEM AND METHOD

(71) Applicant: CareFusion 303, Inc., San Diego, CA (US)

(72) Inventors: Donald Halbert, San Diego, CA (US); Gregory Borges, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 778 days.

(21) Appl. No.: 13/944,828

(22) Filed: Jul. 17, 2013

(65) Prior Publication Data

US 2015/0025497 A1    Jan. 22, 2015

(51) Int. Cl.
*A61M 31/00* (2006.01)
*A61M 5/142* (2006.01)
*A61M 5/168* (2006.01)

(52) U.S. Cl.
CPC ..... *A61M 5/14212* (2013.01); *A61M 5/14228* (2013.01); *A61M 5/16827* (2013.01); *A61M 2005/16863* (2013.01); *A61M 2005/16868* (2013.01)

(58) Field of Classification Search
CPC ......... A61M 2005/14208; A61M 2005/16863; A61M 2005/16868; A61M 5/142; A61M 5/14212; A61M 5/14228; A61M 5/16827; A61M 5/172
USPC ........................................................ 604/506
See application file for complete search history.

(56) References Cited

U.S. PATENT DOCUMENTS

2006/0161376 A1*   7/2006   Hartlaub ........... A61M 5/14276
                                                702/138

* cited by examiner

*Primary Examiner* — Jason Flick
(74) *Attorney, Agent, or Firm* — Fred C. Hernandez; Mintz Levin Cohn Ferris Glovsky and Popeo, P.C.

(57) ABSTRACT

A patient care system is configured for infusing fluid to a patient. The system includes at least one fluid infusion pump connected to a respective fluid supply for pumping the contents of a fluid supply to a patient via fluid supply lines. The system includes a programming module that determines the efficiency of the fluid infusion pumps and dynamically adapts the infusion pumps based on one or more system parameters.

9 Claims, 4 Drawing Sheets

ADAPTIVE VOLUME PER MOTOR REVOLUTION SYSTEM AND METHOD

BACKGROUND

A patient in a hospital often has the need to be infused with one or more fluids, including a variety of drugs. This can require the use of at least one infusion pump. In addition, the infusion pump can be programmed to deliver the one or more fluids to the patient at a variety of infusion rates.

A hospital patient often has the need for multiple intravenous (IV) infusions from multiple supplies of fluids, such as drugs. This can require the use of multiple infusion pumps that are connected to the patient and to fluid containers via fluid lines. In addition, each fluid infusion pump can be programmed to pump fluid to the patient at a variety of infusion rates. The infusion rates can depend on a number of factors including type of fluid, such as drugs, and the needs of the patient.

It can also be important to maintain the programmed infusion rates in order to ensure that the patient being infused with the fluids is not receiving too much or not enough of the fluid. In some instances, the patient can be harmed if given too much or not enough of a recommended dose of fluid. Additionally, in some cases, if the patient receives too much or not enough of a fluid the patient can be severely injured and can be negatively affected. Therefore, it can be critical that patients receive the proper amount of fluid.

Infusion pumps can provide a way to deliver a fluid to a patient at a programmed infusion rate. However, a variety of factors can cause the infusion pump to become more or less efficient such that the programmed infusion rate is disturbed. For example, due to changes in pressure in the fluid lines, more or less fluid per pumping action of the infusion pump can result in more or less fluid delivered to the patient than what was programmed to be delivered.

In view of the foregoing, there is a need for methods and devices for adapting the pumping mechanism of an infusion system in order to maintain a programmed infusion rate.

SUMMARY

Disclosed is a patient care system for infusing fluid to a patient. The system includes one or more fluid infusion pumps, each of which is connected to a respective fluid supply for pumping the contents of a fluid supply to a patient via one or more fluid supply lines. The system can include at least one pressure sensor, including pressure sensors positioned upstream and downstream of the fluid infusion pumps, which can sense pressure along at least the fluid lines to and from the fluid infusion pumps. In addition, one or more system parameters can be evaluated and input into an algorithm which the system can use to determine an efficiency of one or more pumping mechanisms of the fluid infusion pumps. The system can then use the determined efficiencies to dynamically adapt, as necessary, the pumping mechanisms in order to pump fluid at a programmed infusion rate. For example, the system may adapt or otherwise adjust volume of fluid dispenses or pumped per rotation of a pump motor mechanism.

In one aspect, there is disclosed a method for determining an efficiency of a pumping mechanism of an infusion pump and dynamically adapting the pumping mechanism based on the efficiency, the method comprising: programming the pumping mechanism to deliver a fluid at an infusion rate wherein the pumping mechanism is configured to deliver the fluid along a fluid line from a fluid supply to a patient and communicates with a programming module having a processor and at least one algorithm which inputs one or more system parameters for determining the efficiency of the pumping mechanism; inputting the one or more system parameters into the at least one algorithm; processing the algorithm to determine the efficiency of the pumping mechanism; and dynamically adapting the pumping mechanism based on the efficiency of the pumping mechanism.

In another aspect, there is disclosed a patient care system for infusing a medical fluid, the patient care system comprising: a fluid supply adapted to hold a medical fluid; a fluid line providing fluid communication between the fluid supply and a patient; a pumping mechanism controlling fluid flow along the fluid line between the fluid container and the patient; a plurality of pressure sensors configured to sense pressure in the fluid line; and a programming module in communication with the pumping mechanism and configured to dynamically adapt the pumping mechanism based on an efficiency of the pumping mechanism, and wherein the programming module has a processor and one or more algorithms for determining the efficiency of the pumping mechanism.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

Disclosed is a patient care system for infusing fluid to a patient. The system includes one or more fluid infusion pumps, each of which is connected to a respective fluid supply for pumping the contents of a fluid supply to a patient via one or more fluid supply lines. The system can include at least one pressure sensor, including pressure sensors positioned upstream and downstream of the fluid infusion pumps, which can sense pressure along at least the fluid lines to and from the fluid infusion pumps. In addition, one or more system parameters can be evaluated and input into an algorithm which the system can use to determine an efficiency of one or more pumping mechanisms of the fluid infusion pumps. The system can then use the determined efficiencies to dynamically adapt, as necessary, the pumping mechanisms in order to pump fluid at a programmed infusion rate. For example, the system may adapt or otherwise adjust volume of fluid dispenses or pumped per rotation of a pump motor mechanism.

Figure 1:
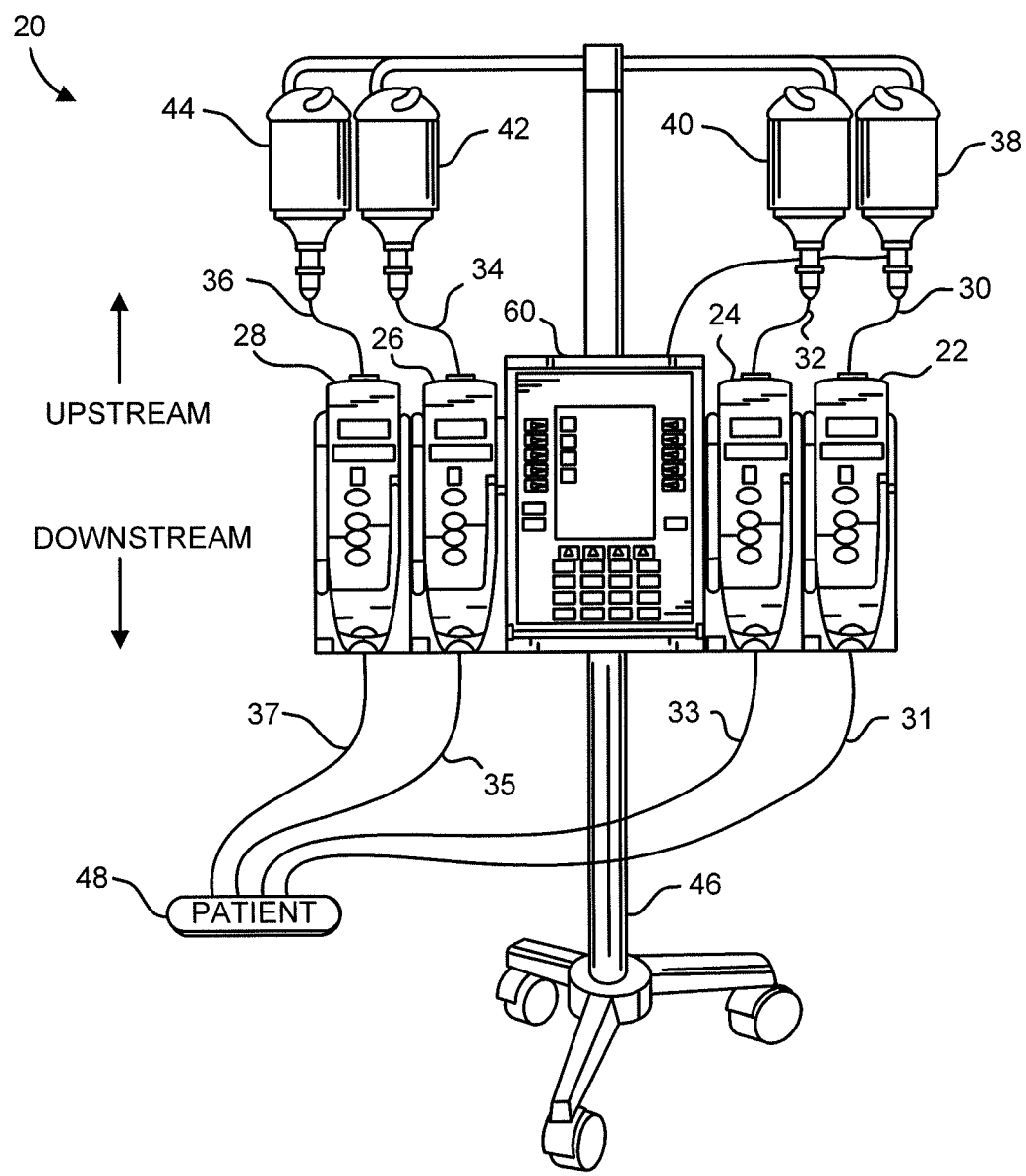
FIG. 1 is a front view of a patient care system having four fluid infusion pumps, each of which is connected to a respective fluid supply for pumping the contents of the fluid supply to a patient.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as tubing, through which fluid can flow through.

Fluid supplies 38, 40, 42, and 44, which may take various forms but in this case are shown as bottles, are inverted and suspended above the infusion pumps 22, 24, 26 and 28. Fluid supplies may also take the form of bags or other types of containers. Both the patient care system 20 and the fluid supplies 38, 40, 42, and 44 are mounted to a roller stand or IV pole 46.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other.

Typically, medical fluid administration sets have more parts than are shown in FIG. 1. Many have check valves, drip chambers, valved ports, connectors, and other devices well known to those skilled in the art. These other devices have not been included in the drawings so as to preserve clarity of illustration.

It should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater.

Figure 2:
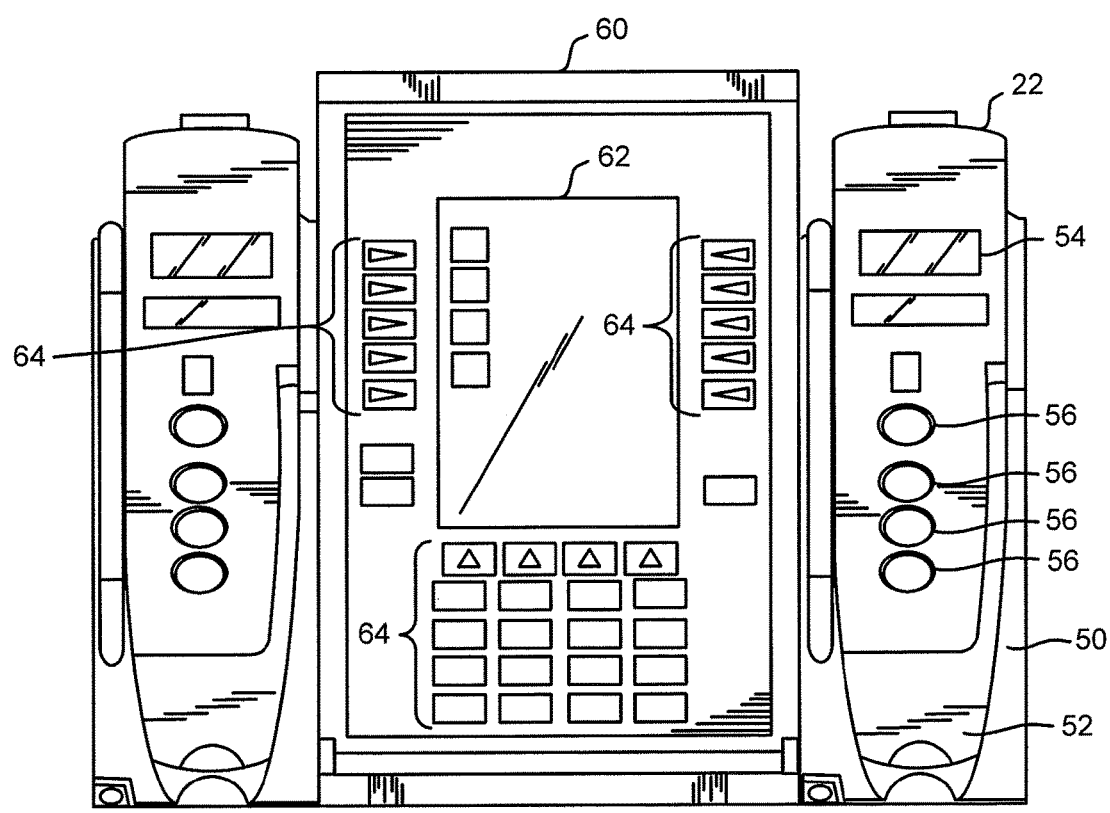
FIG. 2 is an enlarged view of a portion of the patient care system of FIG. 1 showing two of the fluid infusion pumps mounted at either side of a programming module, and the displays and control keys of each, with the programming module being capable of programming both infusion pumps.

Referring now to FIG. 2, an enlarged view of the front of the infusion pump 24 is shown. The pump includes a front door 50 and a handle 52 that operates to lock the door in a closed position for operation and to unlock and open the door for access to the internal pumping and sensing mechanisms and to load administration sets for the pump. When the door is open, the tube can be connected with the pump. When the door is closed, the tube can be brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). Control keys 56 exist for programming and controlling operations of the infusion pump as desired, including programming an infusion rate. The infusion pump 22 also includes audio alarm equipment in the form of a speaker (not shown).

In the embodiment shown, a programming module 60 is attached to the left side of the infusion pump 22. Other devices or modules, including another infusion pump, may be attached to the right side of the infusion pump 22, as shown in FIG. 1. In such a system, each attached pump represents a pump channel of the overall patient care system 20. In one embodiment, the programming module 60 is used to provide an interface between the infusion pump 22 and external devices as well as to provide most of the operator interface for the infusion pump 22.

In addition, the programming module 60 can assist in programming the infusion rate of the infusion pump 22, or any infusion pump in communication with the programming module 60. The programming module 60 can assist in monitoring any part of the patient care system 20, including the one or more pressure sensors, in order to ensure the patient care system 20 is providing effective care to the patient. Additionally, the programming module 60 can assist in ensuring that the proper amount of one or more fluids are being delivered to the patient at the programmed infusion rate.

For example, the programming module 60 can accept or input one or more sensed system parameters into an algorithm 110 (FIG. 4) which can allow the programming module to determine the efficiency of the pumping mechanism. Based on the determined efficiency, the programming module 60 can dynamically adapt the pumping mechanism to the sensed system parameters in order to ensure the amount of fluid pumped to the patient over time is at least approximately equal to the programmed infusion rate. This can assist in minimizing variability in the amount of fluid volume dispensed to the patient. In addition, in some embodiments, the programming module 60 can process the algorithm 110 at least prior to starting pumping in order to compensate for system parameters. Additionally, the programming module 60 can continually process the algorithm 110 throughout the pumping process in order to monitor and dynamically adapt, as necessary, the pumping mechanism 70 to changing system parameters.

The programming module 60 can include a display 62 for visually communicating various information, such as the operating parameters of the pump 22 and alert indications and alarm messages. The programming module 60 may also include a speaker to provide audible alarms. The programming module can also have various input devices, including control keys 64 and a bar code scanner (not shown) for scanning information relating to the infusion, the patient, the care giver, or other. The programming module also has a communications system (not shown) with which it may communicate with external equipment such as a medical facility server or other computer and with a portable processor, such as a handheld portable digital assistant ("PDA"), or a laptop-type of computer, or other information device that a care giver may have to transfer information as well as to download drug libraries to a programming module or pump. In addition, the programming module 60 can communicate with some external equipment which can provide sensed system parameters, such as fluid line pressure, changes in infusion rate, and the height or vertical positioning of the fluid supply relative to the pump.

FIG. 2 includes a second pump module 26 connected to the programming module 60. As shown in FIG. 1, more pump modules may be connected. Additionally, other types of modules may be connected to the pump modules or to the programming module 60.

Figure 3:
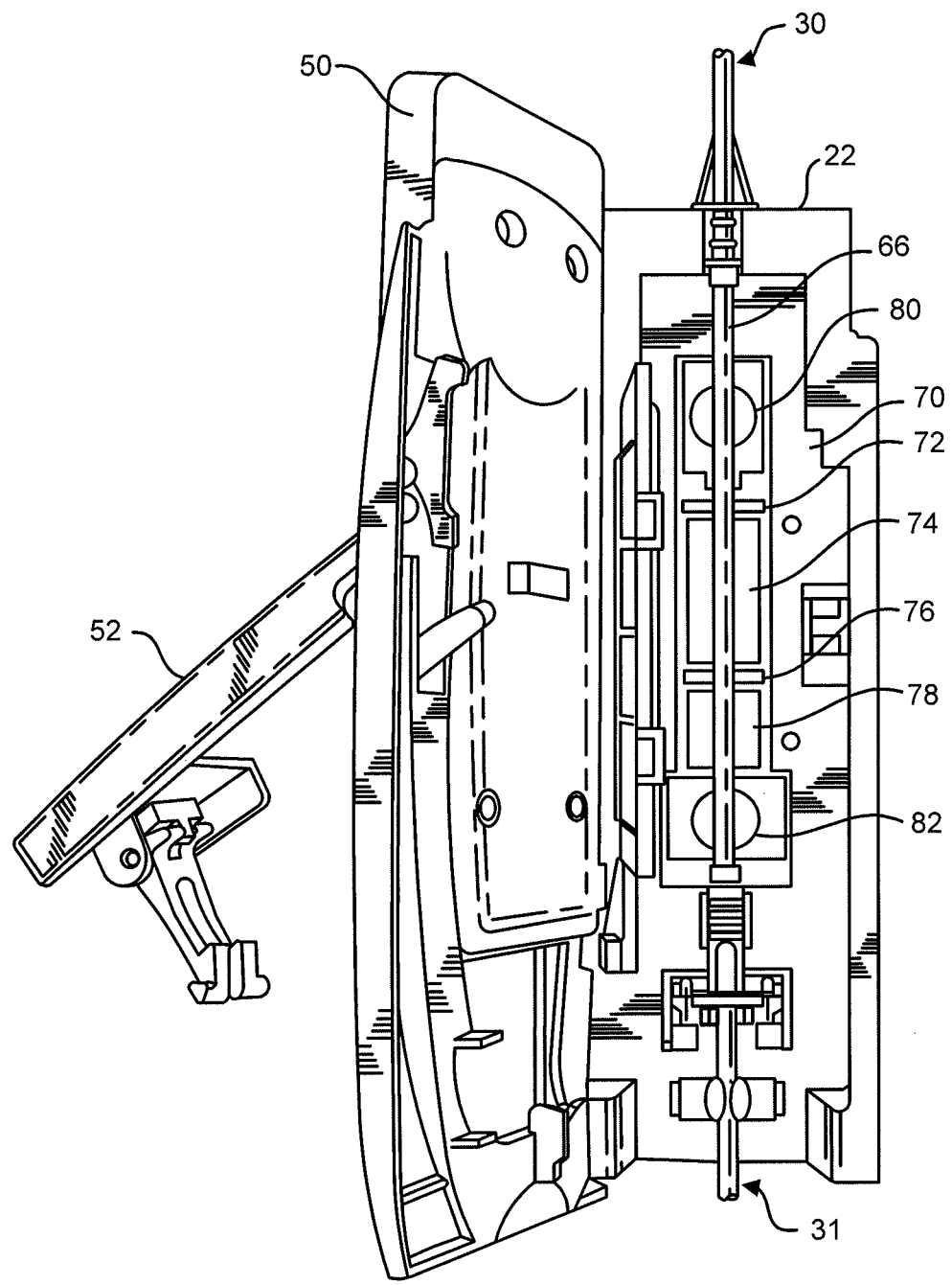
FIG. 3 is a perspective view of one of the fluid infusion pumps of FIGS. 1 and 2 with its front door open.

Turning now to FIG. 3, an infusion pump 22 is shown in perspective view with the front door 50 open, showing the upstream fluid line 30 and downstream fluid line 31 in operative engagement with the pump 22. The infusion pump 22 directly acts on a tube 66 that connects the upstream fluid line 30 to the downstream fluid line 31 to form a continuous fluid conduit, extending from the respective fluid supply 38 to the patient 48 (see FIG. 1), through which fluid is acted upon by the pump to move fluid downstream to the patient. Specifically, a pumping mechanism 70 acts as the flow control device of the pump to move fluid though the conduit. It should be appreciated that various types of pumping mechanisms may be used including displacement pumping mechanisms. In addition, the pump does not necessarily directly act on the tube.

Figure 4:
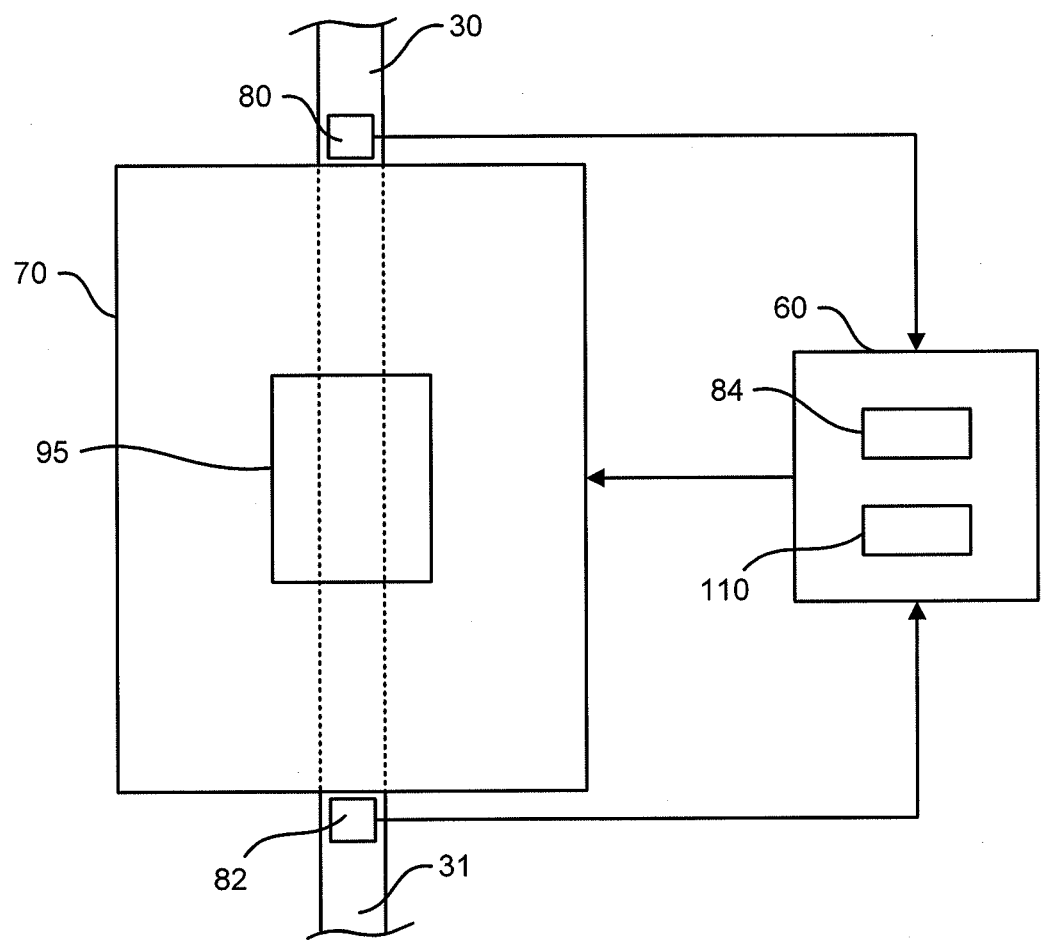
FIG. 4 is a block diagram showing components of one embodiment of the patient care system.

As shown in FIG. 4, the pumping mechanism 70 can include a motor 95 which can be configured to assist in pumping a defined volume of fluid from the pumping mechanism for every rotation or mechanical cycle of the motor 95. Therefore, the infusion rate of the pumping mechanism 70 can be at least partially controlled by the motor rotation rate or mechanical cycle rate of the motor 95. In addition, the effective infusion rate can be controlled by increasing and decreasing the motor rotation rate.

The pumping mechanism 70 can have any number of motors 95 which can have any number of mechanisms which perform a mechanical cycle. The rate at which the mechanical cycle, such as a motor rotation, is performed can affect the amount of fluid that is pumped from the pumping mechanism 70. However, although each mechanical cycle can be configured to pump a defined amount of fluid from the pumping mechanism 70, a number of system parameters can affect the efficiency of the pumping mechanism 70. For example, one or more system parameters can lower the efficiency of the pumping mechanism 70 such that the amount of fluid actually pumped from the pumping mechanism 70 with each mechanical cycle is lower than the amount of fluid the pumping mechanism 70 was designed or configured to pump. Therefore, it can be advantageous to monitor at least one system parameter in order to determine the efficiency of the pumping mechanism and dynamically adapt the pumping mechanism 70 can compensate for the monitored system parameters.

In some embodiments, the pumping mechanism 70 may be of the "four finger" type and can include an upstream occluding finger 72, a primary pumping finger 74, a downstream occluding finger 76, and a secondary pumping finger 78, as shown in FIG. 3. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIGS. 3 and 4 further show a downstream pressure sensor 82 included in the infusion pump 22 embodiment at a downstream location with respect to the pumping mechanism 70 and motor 95. For example, the downstream pressure sensor 82 can be located between the patient 48 (FIG. 1) and the pumping mechanism 70.

In some embodiments, the downstream pressure sensor 82 can affect the efficiency of the pumping mechanism 70. Therefore, the downstream pressure sensor 82 can provide fluid pressure readings of the downstream fluid line 31 to the programming module 60 which can use the sensed pressure readings to ensure that the actual infusion rate delivered to the patient is at least approximately equal to the programmed infusion rate. For example, the downstream pressure sensor 82 can provide sensed pressure readings to the programming module 60 which can enter them into one or more algorithms 110 for determining the efficiency of the pumping mechanism. In addition, based on the determined efficiency, the programming module 60 can dynamically adapt the pumping mechanism, as necessary, so that the programmed infusion rate is ensured.

With reference still to FIG. 3, an upstream pressure sensor 80 may also be included in the pump 22 embodiment at an upstream location with respect to the pumping mechanism 70 and motor 95. The upstream pressure sensor 80 can be located upstream from the pumping mechanism 70 and motor 95, that is, at a location between the fluid supply 38 (FIG. 1) and the pumping mechanism 70.

In some embodiments, a change in upstream pressure can affect the efficiency of the pumping mechanism 70. Therefore, the upstream pressure sensor 80 can provide fluid pressure readings of the upstream fluid line 30 to the programming module 60 which can use the sensed pressure readings to ensure that the actual infusion rate delivered to the patient is at least approximately equal to the programmed infusion rate. For example, the upstream pressure sensor 80 can provide sensed pressure readings to the programming module 60 which can enter them into one or more algorithms 110 for determining the efficiency of the pumping mechanism. In addition, based on the determined efficiency, the programming module 60 can dynamically adapt the pumping mechanism 70, as necessary, so that the programmed infusion rate is ensured.

The one or more downstream pressure sensors 82 and upstream pressure sensors 80 may take many forms well known to those skilled in the art, including a piezoresistive device. Consequently, no further technical details concerning the mechanical formation of the sensor are presented herein. The downstream pressure sensors 82 and upstream pressure sensors 80 can provide pressure signals in response to pressure sensed in the downstream fluid line 31 and upstream fluid line 30, respectively, of the fluid conduit 66. Those pressure signals can be analog in form and can be converted to digital form by an analog-to-digital converter ("A/D") integral with the sensor or by an A/D located elsewhere in the data stream.

In some embodiments, the pressure signals can be supplied to a processor 84 of the programming module 60. In accordance with its programming, the processor can be configured to receive the pressure signals and process them to detect pressure levels and pressure changes. In accordance with an aspect of the invention, the processor can be configured to detect static and changing pressure in at least one of the downstream fluid line 31 and upstream fluid line 30 and use one or more algorithms 110 to determine, for example, the efficiency of one or more pumping mechanisms 70.

In addition, other factors or system parameters such as changes in infusion rate and the height of the fluid source relative to the pumping mechanism 70 can be supplied to the processor of the programming module 60 in order to determine the efficiency of the pumping mechanism 70. As discussed above, the programming module 60 can use the determined efficiency of the pumping mechanism to dynamically adapt, as necessary, the pumping mechanism 70 in order to compensate for the system parameters and minimize the variability in the volume dispensed.

It is generally desirable to program the fluid pumps so that they deliver a specific amount of fluid, such as from the fluid supplies, over a specific amount of time to the patient. In particular, it can be beneficial to have at least one drug delivered or infused to the patient. However, the one or more drugs which can be beneficial when delivered to a patient can be most effective when delivered at a specific infusion rate. Moreover, the one or more drugs can be either harmful or ineffective if delivered to the patient at an undesirable rate, such as an infusion rate that is more or less than what the infusion pump was programmed to deliver.

The efficiency of the pumping mechanism 70 can depend on a number of system parameters which can be sensed by any number of sensing mechanisms and input into the algorithm 110 for processing by the processor 84. For example, a change in pressure in the upstream fluid line 30 or downstream fluid line 31 can affect the efficiency of the pumping mechanism which can result in the actual rate of fluid being delivered to the patient to be more or less than the programmed infusion rate. In some instances, the change in pressure in either the upstream fluid line 30 or downstream fluid line 31 can be a result of change in temperature or change in tubing compliance. Additionally, the pressure in the downstream fluid line 31 can change depending on changing conditions on the patient end of the downstream fluid line 31. For example, blood clotting or change in blood viscosity can affect the rate at which the fluid can dispense from the downstream fluid line 31 which can result in an increase in fluid pressure.

Other factors can affect the efficiency of the pumping mechanism, including the height of the fluid supply 38 relative to the infusion pump 22. For example, a change in the height differential between the fluid supply 38 and the infusion pump 22 can result in a change in pressure in the upstream fluid line 30 which can change the efficiency of the pumping mechanism 70. One or more sensors can be implemented in the system in order to provide the programming module 60 with system parameter data relating to the fluid supply height differential. For example, the sensors can either sense the upstream fluid line 30 or fluid supply height differential which can be sent to the programming module 60 for processing, such as inputting the data into one or more algorithms 110.

In some embodiments, a change in infusion rate can affect the efficiency of the pumping mechanism 70. For example, as the infusion rate increases the pumping mechanism 70 can lose efficiency. Therefore, in some embodiments, the programming module 60 can determine the efficiency of the pumping mechanism 70 each time the infusion rate changes, including when the infusion rate is first programmed, in order to continually monitor the efficiency of the pumping mechanism 70 and dynamically adapt, as necessary, the mechanical cycle rate of the pumping mechanism based on the infusion rate. In addition, the programming module 60 can include one or more algorithms 110 which can input the infusion rate in order to determine the efficiency of the pumping mechanism 70.

Some embodiments of the programming module 60 can include one or more algorithms 110 which can simultaneously and continuously monitor the one or more system parameters, including the infusion rate, fluid line pressures, and fluid supply height differential, as discussed above. In addition, the one or more algorithms 110 can determine the efficiency of the pumping mechanism 70. Therefore, the programming module 60 can continually determine the efficiency of the pumping mechanism 70 and dynamically adapt the pumping mechanism 70, such as the motor 95, based on the efficiency of the pumping mechanism. This can assist in ensuring that the actual amount of fluid delivered to the patient is at least approximately equal to the programmed infusion rate which can provide the patient with optimal care with respect to the delivery of fluids.

Any number of factors or system parameters can affect the efficiency of the pumping mechanism 70 and the programming module 60, including the algorithms 110, can be configured to receive input data relating to any number of factors or system parameters for determining the efficiency of the pumping mechanism.

The processor can be in communication with one or more pumps or pumping mechanisms 70 and it should be understood that other embodiments may exist in which multiple pump channels associated with a multi-channel patient care system may be monitored by the same processor. In such an embodiment, the processor performs the same functions for each pump channel of the system. As an example, FIG. 1 shows a four pump system in which the four pumps 22, 24, 26, and 28 are connected to a common programming module 60 having an internal processor. The processor of the programming module 60 may perform the "infusion rate maintenance" for all four pumps.

Pumping mechanism efficiencies at a variety of system characteristics or other reference values for evaluating the efficiency of the pumping mechanism may be stored in a memory which can be included in the programming module and which the processor can access. The programs and algorithms of the processor, including the program supporting the dynamic adaptation of the pumping mechanism for infusion rate maintenance, may be stored in the same memory, or in another memory. Use of memory to store programs and data is well known and no further details are provided here. Values and other programming may also be input into the memory using an input device, such as control keys, or may be preprogrammed.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A method for determining an efficiency of a pumping mechanism of an infusion pump and dynamically adapting the pumping mechanism based on the efficiency, the method comprising:
   connecting an external pumping mechanism to a patient at an extracorporeal connection location of the patient;
   programming the pumping mechanism to deliver a fluid at an infusion rate wherein the pumping mechanism is configured to deliver the fluid along a fluid line from a fluid supply to a patient and communicates with a programming module having a processor and at least one algorithm which inputs one or more system parameters for determining the efficiency of the pumping mechanism;
   sensing a first pressure at a location of the fluid line upstream of the pumping mechanism and external to the patient using a first pressure sensor positioned upstream of the pumping mechanism and external to the patient;
   sensing a second pressure at a location of the fluid line downstream of the pumping mechanism and external to the patient using a second pressure sensor positioned downstream of the pumping mechanism and external to the patient;
   inputting the first pressure, the second pressure, and one or more system parameters into the at least one algorithm;
   processing the algorithm to determine the efficiency of the pumping mechanism; and
   dynamically adapting the pumping mechanism based on the efficiency of the pumping mechanism.

2. The method of claim 1, wherein the system parameters include at least one or more of a change in infusion rate, and a height differential between the fluid supply and the pumping mechanism.

3. The method of claim 2, wherein the at least one pressure sensor is positioned along the fluid line at least one of between the pumping mechanism and the patient and between the fluid supply and the pumping mechanism.

4. The method of claim 1, wherein dynamically adapting the pumping mechanism based on the efficiency of the pumping mechanism causes a rate of the fluid actually delivered to the patient to be equal to the programmed infusion rate.

5. The method of claim 1, wherein the pumping mechanism includes a motor configured to pump a volume of fluid for every mechanical cycle of the motor.

6. The method of claim 5, wherein dynamically adapting the pumping mechanism comprises increasing or decreasing a rate at which the motor performs the mechanical cycle.

7. The method of claim 6, wherein the mechanical cycle includes a motor rotation.

8. The method of claim 1, wherein the processor is configured to simultaneously process more than one algorithm including more than one system parameter and determine the efficiency of the pumping mechanism.

9. The method of claim 1, wherein the programming module is configured to dynamically alter infusion rates of more than one infusion pump in communication with the programming module.

* * * * *